United States Patent
Watanabe et al.

(10) Patent No.: US 10,413,177 B2
(45) Date of Patent: Sep. 17, 2019

(54) EYEBALL OBSERVATION DEVICE, EYEWEAR TERMINAL, LINE-OF-SIGHT DETECTION METHOD, AND PROGRAM

(71) Applicant: SONY CORPORATION, Tokyo (JP)

(72) Inventors: Sayaka Watanabe, Tokyo (JP); Yuhi Kondo, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/571,997

(22) PCT Filed: Jul. 14, 2016

(86) PCT No.: PCT/JP2016/070801
§ 371 (c)(1),
(2) Date: Nov. 6, 2017

(87) PCT Pub. No.: WO2017/014137
PCT Pub. Date: Jan. 26, 2017

(65) Prior Publication Data
US 2018/0140187 A1    May 24, 2018

Related U.S. Application Data

(63) Continuation-in-part of application No. PCT/JP2016/062450, filed on Apr. 20, 2016.

(30) Foreign Application Priority Data

Jul. 17, 2015   (JP) ................................. 2015-142619

(51) Int. Cl.
  *A61B 3/113*   (2006.01)
  *A61B 3/14*    (2006.01)
  *G06K 9/00*    (2006.01)

(52) U.S. Cl.
  CPC ............... *A61B 3/113* (2013.01); *A61B 3/14* (2013.01); *G06K 9/00604* (2013.01)

(58) Field of Classification Search
  CPC ......... A61B 3/113; A61B 3/14; A61B 3/1015; A61B 3/1025; A61B 3/0008; A61B 3/0025; G06K 9/00; G06K 9/00604
  USPC ....... 351/205, 206, 208, 209, 210, 220, 221, 351/246
  See application file for complete search history.

(56) References Cited

U.S. PATENT DOCUMENTS

| | | | | |
|---|---|---|---|---|
| 5,345,281 A * | 9/1994 | Taboada | ................. | A61B 3/113 351/209 |
| 7,280,678 B2 * | 10/2007 | Haven | .................... | A61B 3/113 348/78 |
| 2014/0268053 A1 * | 9/2014 | Fabian | .................. | A61B 3/152 351/208 |
| 2016/0081547 A1 * | 3/2016 | Gramatikov | ....... | G06K 9/00604 351/210 |

* cited by examiner

*Primary Examiner* — Jie Lei
(74) *Attorney, Agent, or Firm* — Paratus Law Group, PLLC

(57) ABSTRACT

There is provided an eyeball observation device, which can stably detect a line of sight, the eyeball observation device including: at least one infrared light source configured to radiate polarized infrared light onto an eyeball of a user; and at least one imaging device configured to capture an image of the eyeball irradiated with the polarized infrared light and to be capable of simultaneously capturing a polarization image with at least three directions.

14 Claims, 11 Drawing Sheets

EYEBALL OBSERVATION DEVICE, EYEWEAR TERMINAL, LINE-OF-SIGHT DETECTION METHOD, AND PROGRAM

CROSS REFERENCE TO PRIOR APPLICATION

This application is a National Stage Patent Application of PCT International Patent Application No. PCT/JP2016/070801 (filed on Jul. 14, 2016) under 35 U.S.C. § 371, which is a continuation-in-part of PCT International Patent Application No. PCT/JP2016/062450 (filed on Apr. 20, 2016), which claims priority to Japanese Patent Application No. 2015-142619 (filed on Jul. 17, 2015), which are all hereby incorporated by reference in their entirety.

TECHNICAL FIELD

The present disclosure relates to an eyeball observation device, an eyewear terminal, a line-of-sight detection method, and a program.

BACKGROUND ART

A corneal reflection method has been widely used as a technology for inferring a direction of a line of sight. In the corneal reflection method, a direction of a line of sight is inferred using a reflection image formed on a surface of a cornea of an eyeball obtained by radiating infrared light onto the eyeball (which will also be referred to as a "corneal reflection image" below) or an image obtained by imaging a pupil thereof using infrared light. However, when a direction of a line of sight of a user wearing glasses is to be inferred, infrared light radiated onto the user's eyeball is reflected on a surface of the glasses, and a reflection image thereof serves as an outlier (a pseudo bright spot) which hinders a corneal reflection image or a pupil from being observed.

Thus, Patent Literature 1 discloses, for example, a method of removing an outlier other than a corneal reflection image by controlling on- and off-states of a voltage of a liquid crystal panel on a front side of an imaging device to cause only light with a predetermined polarization direction or light beams with all polarization directions to be transmitted therethrough.

In addition, individuals can be identified as in iris authentication or awakened states or health states of individuals can be ascertained by imaging eyeballs and performing image processing on the images. However, in a case in which infrared light is radiated toward a user who is wearing glasses, light reflected on a surface of the glasses becomes an outlier, and thus it may be difficult to observe the user's pupil, iris, and the like, as in a case in which a direction of a line of sight is to be inferred.

CITATION LIST

Patent Literature

Patent Literature 1: JP 3297504B

DISCLOSURE OF INVENTION

Technical Problem

However, in the above-described Patent Literature 1, it is necessary to install a light source such that an incidence angle of light from the light source approximates a Brewster's angle and a degree of polarization of corneal reflection is large. Since the incidence angle varies depending on a positional relation between an eyeball and the light source or a direction of a line of sight, an outlier is considered to be removable only in a case in which a specific condition is satisfied. In addition, in order to infer a direction of a line of sight, positions of a corneal reflection image and a pupil at a certain moment are necessary. In order to trace fast movements of an eyeball, it is necessary to perform switching of a pressurized state of a liquid crystal panel and imaging at a sufficiently high frequency and to achieve synchronization thereof. However, if a shutter speed of an imaging device increases, it is difficult to detect a pupil due to a reduced amount of light. Furthermore, since it is necessary to set polarization directions of the light source and the imaging device to perfectly coincide with each other, an installation error between a polarizer, the imaging device, and the light source should be minimized as much as possible. In addition, if the liquid crystal panel is disposed in front of the light source and the imaging device, a size of an eyeball observation device increases.

Therefore, the present disclosure proposes a novel and improved eyeball observation device, eyewear terminal, line-of-sight detection method, and program which enable an image of an eyeball to be stably acquired.

Solution to Problem

According to the present disclosure, there is provided an eyeball observation device including: at least one infrared light source configured to radiate polarized infrared light onto an eyeball of a user, and at least one imaging device configured to capture an image of the eyeball irradiated with the polarized infrared light and to be capable of simultaneously capturing a polarization image with at least three directions.

In addition, according to the present disclosure, there is provided an eyewear terminal including: a lens configured to be provided in front of an eye of a user, and an eyeball observation device including at least one infrared light source configured to radiate polarized infrared light onto an eyeball of the user and at least one imaging device configured to capture an image of the eyeball irradiated with the polarized infrared light and to be capable of simultaneously capturing a polarization image in at least three directions.

Further, according to the present disclosure, there is provided a line-of-sight detection method including: capturing an image of an eyeball of a user irradiated with infrared light polarized with respect to the eyeball by at least one infrared light source and simultaneously acquiring a polarization image with at least three directions; generating a polarization model representing a relation between a polarization direction and luminance with respect to each pixel of the polarization image; generating an arbitrary-phase polarization image having an arbitrary polarization direction by using the polarization model; and inferring a direction of a line of sight on the basis of the arbitrary-phase polarization image.

In addition, according to the present disclosure, there is provided a program causing a computer to execute: capturing an image of an eyeball of a user irradiated with infrared light polarized with respect to the eyeball by at least one infrared light source and simultaneously acquiring a polarization image with at least three directions; generating a polarization model representing a relation between a polarization direction and luminance with respect to each pixel of the polarization image; generating an arbitrary-phase polarization image having an arbitrary polarization direction by using the polarization model; and inferring a direction of a line of sight on the basis of the arbitrary-phase polarization image.

Advantageous Effects of Invention

According to the present disclosure described above, a line of sight can be stably detected. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
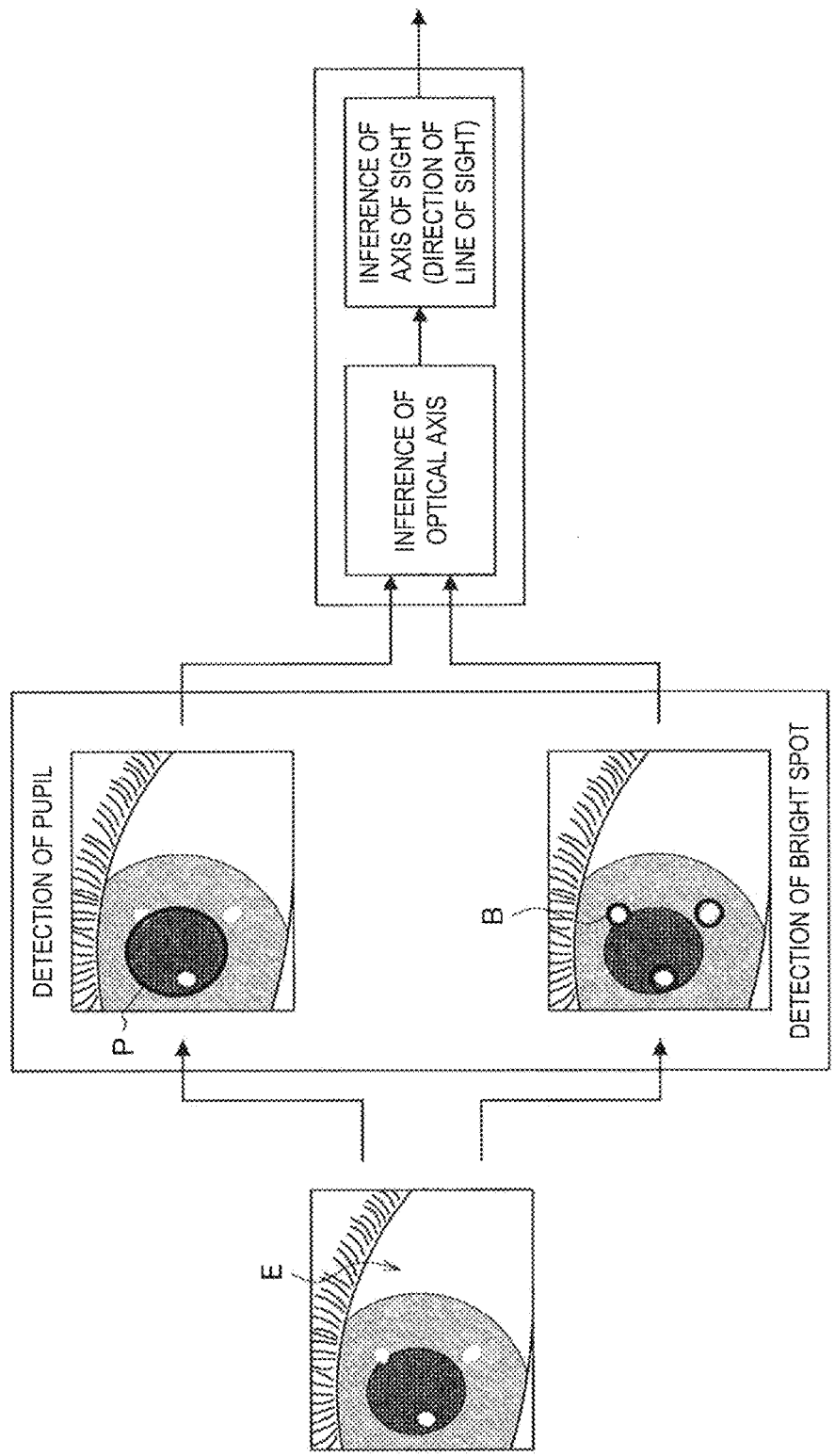
FIG. 1 is an illustrative diagram for describing detection of a pupil and bright spots detected to infer a direction of a line of sight by an eyeball observation device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.

1. Overview
1.1. Schematic configuration of eyeball observation device
1.2. Matters to be described
2. Configurations of devices
2.1. Configuration of eyeball observation device
2.2. Line-of-sight inference arithmetic device
3. Line-of-sight detection method
4. Hardware configuration <1. Overview>

[1.1. Schematic Configuration of Eyeball Observation Device]

First, a schematic configuration of an eyeball observation device according to an embodiment of the present disclosure will be described with reference to FIG. 1. Note that FIG. 1 is an illustrative diagram for describing detection of a pupil and bright spots detected to infer a direction of a line of sight by the eyeball observation device according to the present embodiment. Note that the eyeball observation device may be regarded as a line-of-sight detection device in the present embodiment.

The eyeball observation device according to the present embodiment irradiates an eyeball with polarized infrared light and captures a corneal reflection image of the infrared light to detect a pupil and a bright spot necessary for inferring a direction of a line of sight from the captured image. As illustrated in FIG. 1, a pupil P and a corneal reflection image B of infrared light are detected in an image of an eyeball E captured by an imaging device. The pupil P and the corneal reflection image B are detected using a statistical method such as general machine learning. In addition, the eyeball observation device infers an optical axis using a geometric method and infers an axis of sight (a direction of a line of sight) on the basis of the detected pupil P and corneal reflection image B using a 3-dimensional eyeball model.

[1.2. Matters to be Described]

Here, in detection of a direction of a line of sight of a user wearing glasses in a related art, infrared light radiated on an eyeball is reflected on a surface of the glasses and becomes an outlier such that no pupil and corneal reflection image can be detected, and as a result, it is not possible to stably detect the direction of the line of sight.

In addition, regardless of wearing of glasses, it is difficult to differentiate an outlier of a corneal reflection image (reflection of sun light or an object, sclera reflection of an infrared light source, and pseudo reflection of eyelashes, tears, or the like) from a real corneal reflection image, and in a case in which an outlier exists, accuracy in inference of the line of sight significantly deteriorates.

Meanwhile, in inference of a line of sight using a corneal reflection method, accuracy in inference of the line of sight can be improved if a plurality of light sources are used. A corneal reflection image may not be observed due to a positional relation between a light source, an imaging device, and an eyeball, shapes of an eyelid and an eyeball, a direction of a line of sight, or the like; however, a possibility that a minimum number of corneal reflection images necessary for inferring the line of sight are observed increases if a plurality of light sources are used, and thus the line of sight can be stably inferred. However, in order to infer a line of sight using the plurality of light sources, it is necessary to remove such an above-described outlier and to clearly identify a light source that contributed to generation of a corneal reflection image being observed. However, in a case in which some of a plurality of corneal reflection images are observed, it may also be difficult to precisely identify which light source contributed to the generation of the reflection images.

With regard to reflection of glasses, an eyeball image including a pupil and a cornel reflection image from which only reflection of glasses is removed can be acquired by, for example, polarizing a light source, causing polarized light to pass through a polarization element having an angle orthogonal to an angle of the polarization, and capturing an image thereof (e.g., JP H7-289518A). Here, light transmitted through the glasses is repeatedly reflected and becomes unpolarized light, and thus a bright spot caused by reflection of the glasses and a corneal reflection image can be differentiated with respect to a user wearing glasses. However, the corneal reflection image is originally caused by mirror reflection of a cornea, and polarization does not change when the polarized light is reflected via mirror reflection. That is, the corneal reflection image itself is suppressed only through a polarizer which removes a polarization direction of a light source with respect to a user with naked eyes, similarly to suppression of mirror reflection that may occur on a surface of glasses. In addition, since a light source and an imaging device should be installed such that polarization directions thereof are orthogonal, it is necessary to minimize an installation error between a polarizer, the imaging device, and the light source as much as possible.

To remove an outlier of a corneal reflection image, for example, a method in which bright spots that are in a proper positional relation in accordance with disposition of light sources having reasonable sizes on an image are detected as real corneal reflection images using a plurality of light sources has been proposed (e.g., the specification of JP 4260715B). However, outliers can be reduced to some degree only with the positional relation and the size of the bright spots, but it is not possible to completely remove the outliers.

In addition, it has been proposed that, by controlling on- and off states of a voltage of a liquid crystal panel on a front side of an imaging device to cause only light with a predetermined polarization direction or light beams with all polarization directions to be transmitted therethrough, outliers other than a corneal reflection image can be removed as disclosed in the above-described Patent Literature 1. However, since an incidence angle changes depending on a positional relation between an eyeball and a light source or a direction of a line of sight in the method, outliers are considered to be removable only in a case in which a specific condition is satisfied as described above. In addition, if a shutter speed of the imaging device increases in order to trace fast movements of the eyeball, it is difficult to detect a pupil due to a reduced amount of light. Furthermore, it is necessary to set polarization directions of the light source and the imaging device to perfectly coincide or a size of the eyeball observation device increases if the liquid crystal panel is disposed in front of the light source and the imaging device.

Therefore, an eyeball observation device according to the present embodiment uses at least one infrared polarization light source polarized by a polarizer for radiating infrared light onto an eyeball, and at least one infrared transmitting imaging device that can simultaneously capture polarized light rays with three or more directions. Accordingly, suppression of reflection of glasses, removal of outliers of a corneal reflection image, and identification of corneal reflection images can be achieved, and a pupil and a bright spot to be used in detecting a direction of a line of sight can be detected with high accuracy. A configuration and a function of the eyeball observation device according to the present embodiment will be described in detail below.

<2. Configurations of Devices>

Figure 2:
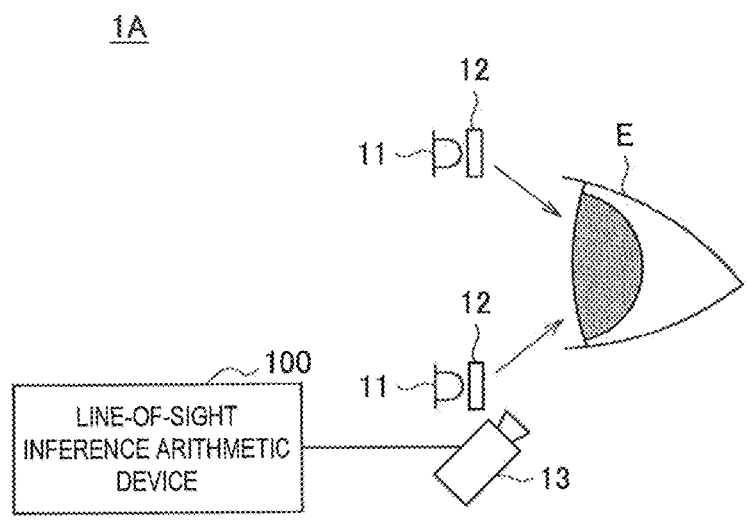
FIG. 2 is a schematic illustrative diagram showing an example of a configuration of the eyeball observation device according to the embodiment.
Figure 3:
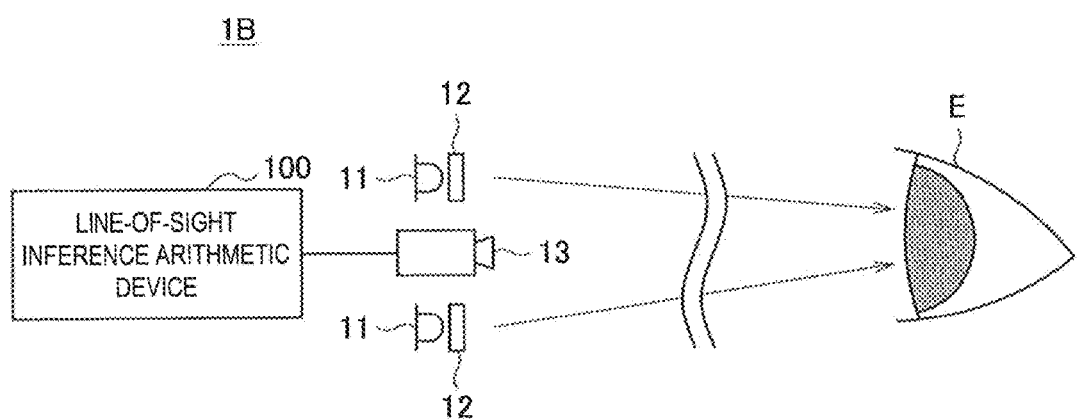
FIG. 3 is a schematic illustrative diagram showing another example of the configuration of the eyeball observation device according to the embodiment.
Figure 4:
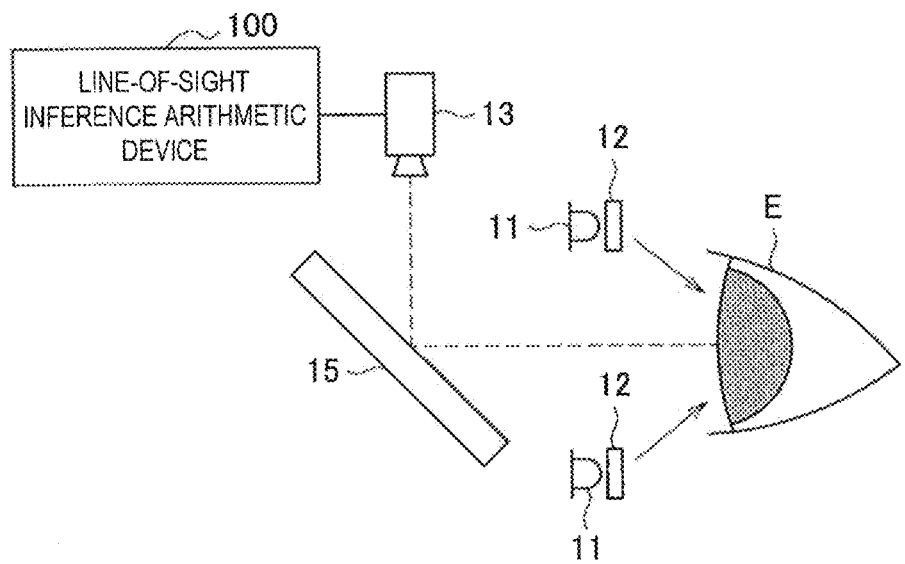
FIG. 4 is a schematic illustrative diagram showing another example of the configuration of the eyeball observation device according to the embodiment.
Figure 5:
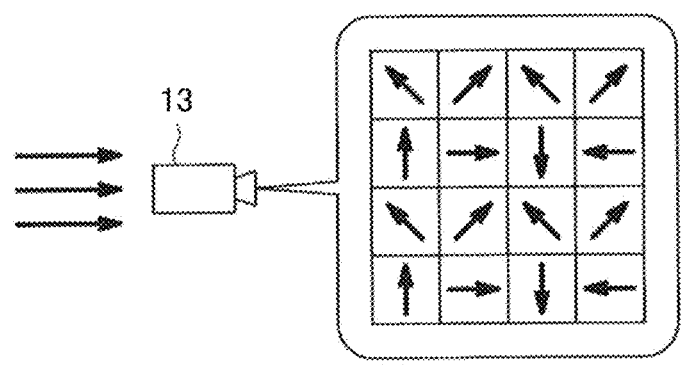
FIG. 5 is an illustrative diagram showing an example of an imaging device used in the eyeball observation device according to the embodiment.

First, examples of hardware configurations of the eyeball observation device 1 according to the present embodiment will be described with reference to FIGS. 2 to 5. Note that FIGS. 2 to 4 are schematic illustrative diagrams showing examples of the configurations of the eyeball observation device 1 (1A to 1C) according to the present embodiment. FIG. 5 is an illustrative diagram showing an example of an imaging device 13 used in the eyeball observation device 1 according to the present embodiment.

[2.1. Configuration of Eyeball Observation Device]

The eyeball observation device 1 (1A to 1C) according to the present embodiment includes infrared light sources 11, polarizers 12, and the imaging device 13, as illustrated in FIGS. 2 to 4. The number of each of the infrared light sources 11, the polarizers 12, and imaging devices 13 provided may be at least one, and a plurality of the constituent elements may be used in principle to improve accuracy in inference of a line of sight. In addition, in a case in which a plurality of polarization directions are used when the line of sight is detected, polarization directions of the polarizers 12 respectively provided corresponding to the infrared light sources 11 may vary from each other.

Each of the infrared light sources 11 is a light source that radiates infrared light onto an eyeball E to obtain corneal reflection, and may be, for example, an infrared LED or the like. Each of the polarizers 12 is an optical element for polarizing the infrared light emitted from the infrared light source 11, which is disposed on an optical path between the infrared light source 11 and the eyeball E.

The imaging device 13 is a device for capturing the eyeball E that is irradiated with the infrared light. The imaging device 13 according to the present embodiment is, for example, a device which can simultaneously perform capturing with three or more polarization directions, as illustrated in FIG. 5 (e.g., the specification of JP 4486703B, the specification of JP 4974543B, etc.). Polarization refers to oscillation of an electric field and a magnetic field of light only in a specific direction. In measurement using the imaging device 13, polarized light traveling in a specific direction is transmitted through the polarizers 12, absorbed, and captured. In addition, since an image of an infrared region is used in inferring a line of sight, a device that can capture infrared regions is used as the imaging device 13. A captured image acquired by the imaging device 13 is output to a line-of-sight inference arithmetic device 100 that infers a direction of the line of sight.

With regard to a positional relation between the eyeball observation device 1 according to the present embodiment and the eyeball E, the eyeball observation device may be disposed at any position as long as the infrared light emitted from the infrared light source 11 and reflected on a cornea is incident on the imaging device 13. For example, as is understood from the eyeball observation device 1A, there may be a configuration in which the infrared light sources 11, the polarizers 12, and the imaging device 13 are disposed in proximity to the eyeball E, as illustrated in FIG. 2. This configuration can be applied to, for example, an eyewear terminal, a head-mounted device, a scouter, and the like of which lenses are set in front of an eye of a user when he or she is wearing the device.

In addition, as is understood from the eyeball observation device 1B illustrated in FIG. 3, for example, there may be a configuration in which the infrared light sources 11, the polarizers 12, and the imaging device 13 may be disposed at positions distant from the eyeball E. This configuration can be applied to, for example, a stationary type terminal disposed distant from an eyeball, such as a display of a television and a personal computer.

Further, as is understood from the eyeball observation device 1C illustrated in FIG. 4, for example, there may be a configuration in which an optical path separation device 15 such as a half mirror is provided between the eyeball E and the imaging device 13. This configuration can be applied to, for example, an electronic viewfinder of a camera and the like.

Note that a configuration of the eyeball observation device 1 according to the present embodiment is not limited to the configurations illustrated in FIGS. 2 to 4, and may be a configuration in which polarized light is radiated onto an eyeball and an image with three polarization directions can be simultaneously captured. In addition, a device to which the eyeball observation device 1 is applied is not limited to the above-described examples, and the device may be, for example, a contact-type device and can be configured to be a device detachable to an eyewear terminal or the like.

[2.2. Line-of-Sight Inference Arithmetic Device]

Next, a functional configuration of the line-of-sight inference arithmetic device 100 of the eyeball observation device 1 according to the present embodiment will be described with reference to FIG. 6. Note that FIG. 6 is a block diagram showing a functional configuration of the line-of-sight inference arithmetic device 100 according to the present embodiment.

Figure 6:
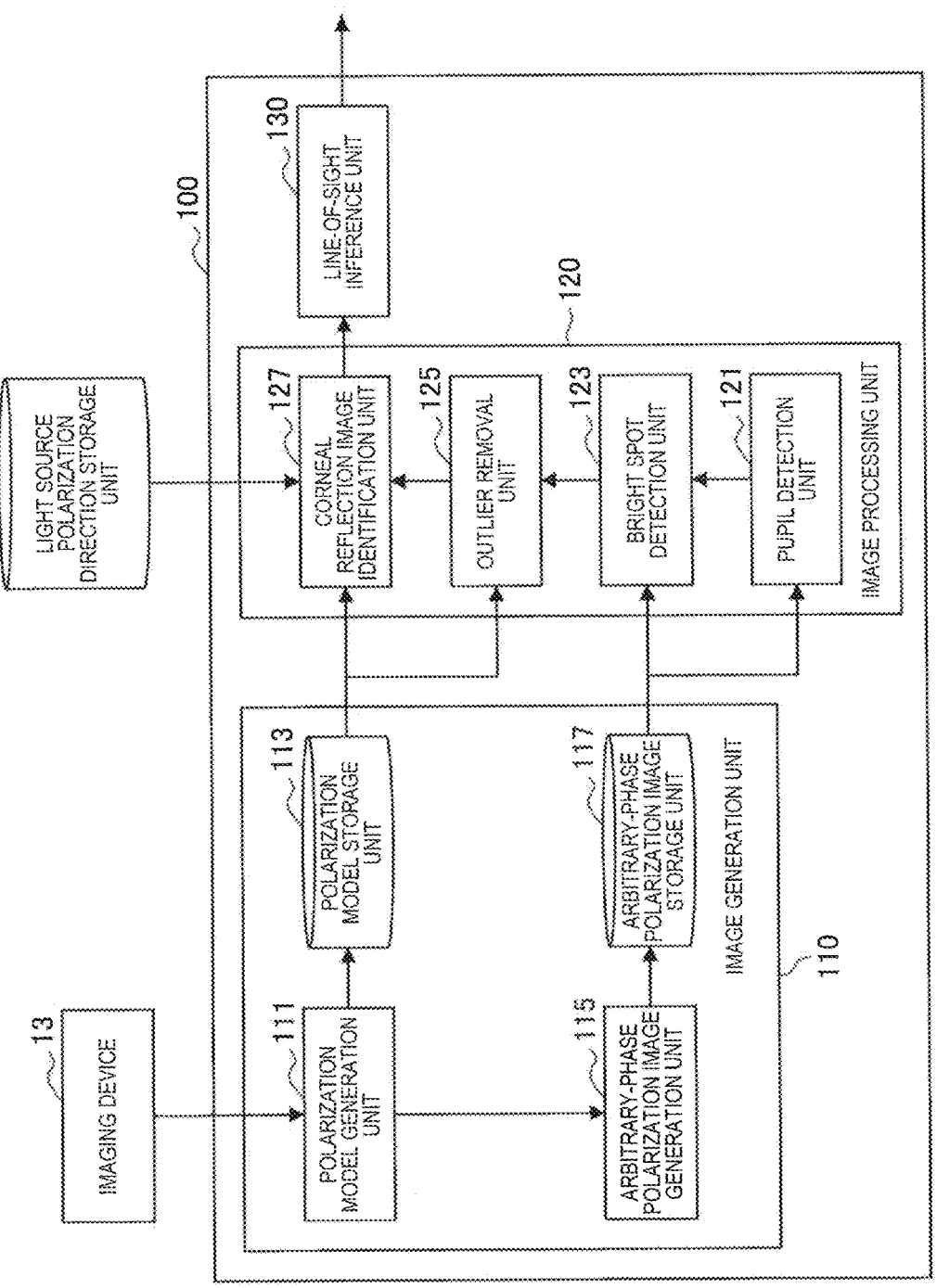
FIG. 6 is a block diagram showing a functional configuration of a line-of-sight inference arithmetic device according to the embodiment.

The line-of-sight inference arithmetic device 100 according to the present embodiment is constituted by an image generation unit 110, an image processing unit 120, and a line-of-sight inference unit 130, as illustrated in FIG. 6.

(Image Generation Unit)

The image generation unit 110 generates a polarization image with a predetermined polarization direction using an image captured by the imaging device 13. The image generation unit 110 is constituted by, for example, a polarization model generation unit 111, a polarization model storage unit 113, an arbitrary-phase polarization image generation unit 115, and an arbitrary-phase polarization image storage unit 117, as illustrated in FIG. 6.

The polarization model generation unit 111 generates a polarization model of each pixel on the basis of the image captured by the imaging device 13. The captured image according to the present embodiment includes polarization in three or more directions. It is known that, if corneal reflection of infrared light emitted via the polarizers 12 is captured, an acquired luminance value and the polarization directions can be modeled using a cosine function shown in Formula (1) which will be described below. Details of the polarization model will be described below. The polarization model generation unit 111 records the generated polarization model of each of the pixels in the polarization model storage unit 113 and outputs the model to the arbitrary-phase polarization image generation unit 115.

The polarization model storage unit 113 is a storage unit that stores the polarization model of each of the pixels generated by the polarization model generation unit 111. The polarization model of each of the pixels stored in the polarization model storage unit 113 is used in, for example, a process of detecting a corneal reflection image which will be described below.

The arbitrary-phase polarization image generation unit 115 generates a polarization image having an arbitrary phase (which will also be referred to as an "arbitrary-phase polarization image" below) on the basis of the polarization model of each of the pixels. The arbitrary-phase polarization image generation unit 115 performs a process of generating an image that is optimal for performing each process in image processing which will be described below. In a case in which a direction of a line of sight of a user wearing glasses is detected, for example, infrared light is reflected on a surface of the glasses and becomes an outlier such that it is not possible to detect a pupil or a bright spot normally. The arbitrary-phase polarization image generation unit 115 generates a polarization image having an optimal phase for performing the detection so that a pupil or a bright spot can be detected normally. Note that details of the process of generating an arbitrary-phase polarization image will be described below. The arbitrary-phase polarization image generation unit 115 records the generated arbitrary-phase polarization image in the arbitrary-phase polarization image storage unit 117.

The arbitrary-phase polarization image storage unit 117 is a storage unit that stores the arbitrary-phase polarization image generated by the arbitrary-phase polarization image generation unit 115. The arbitrary-phase polarization image stored in the arbitrary-phase polarization image storage unit 117 is used in, for example, a process of detecting a pupil or a bright spot which will be described below.

(Image Processing Unit)

The image processing unit 120 performs image processing on the arbitrary-phase polarization image generated by the image generation unit 110 and acquires information necessary for inferring a direction of a line of sight. The image processing unit 120 is constituted by, for example, a pupil detection unit 121, a bright spot detection unit 123, an outlier removal unit 125, and a corneal reflection image identification unit 127, as illustrated in FIG. 6.

The pupil detection unit 121 detects a pupil in a polarization image having a phase appropriate for pupil detection. The pupil detection unit 121 acquires the polarization image having the phase appropriate for pupil detection (which will also be referred to as a "polarization image for pupil detection" below) from the arbitrary-phase polarization image storage unit 117 and detects a pupil in the polarization image for pupil detection. In a case in which the infrared light sources 11 are disposed at positions distant from an optical axis of the imaging device 13, for example, the pupil of the acquired captured image is observed to be black (a dark pupil). Alternatively, in a case in which the infrared light sources 11 are installed at positions very close to the imaging device 13 on the optical axis thereof, the pupil is observed to be white (a bright pupil) due to retroreflection of a retina. Using the above-described features, the pupil detection unit 121 detects, for example, an elliptical black region (or white region) in the polarization image for pupil detection as the pupil. Alternatively, the pupil detection unit 121 may extract a pupil portion from a difference image of the bright pupil and the dark pupil.

The bright spot detection unit 123 detects bright spots in the captured image. The bright spot detection unit 123 detects regions, which have higher luminance values than surrounding regions, sizes equal to or smaller than a predetermined size, and of which detection positions have a predetermined degree or higher of matching with installation positions of the infrared light sources 11, in the image as bright spots. The bright spots detected by the bright spot detection unit 123 also include an outlier such as a pseudo bright spot other than corneal reflection images.

The outlier removal unit 125 removes an outlier such as a pseudo bright spot from the bright spots detected by the bright spot detection unit 123 and detects only the corneal reflection images. The outlier removal unit 125 obtains degrees of polarization of pixels of the bright spot regions detected by the bright spot detection unit 123 using the polarization model stored in the polarization model storage unit 113. Then, the bright spots are divided into real corneal reflection images and outliers on the basis of a degree of polarization. Note that details of the outlier removal process will be described below.

The corneal reflection image identification unit 127 identifies a corresponding infrared light source 11 to ascertain what light source contributed to the generation of the reflection image with respect to the real corneal reflection image specified by the outlier removal unit 125. By using the plurality of infrared light sources 11 to infer a line of sight through corneal reflection, accuracy in inference of the line of sight can be improved or non-observation of the corneal reflection image caused by a position of the line of sight can be prevented. However, in a case in which only some of a plurality of corneal reflection images are observed, it may not be possible to accurately identify a light source that contributed to the generation of the reflection images. Thus, in the present embodiment, a principle of expressing a difference in polarization directions as a phase difference of polarization models is applied such that each of the infrared light sources 11 corresponding to the corneal reflection images is identified. Note that details of a process of identifying corneal reflection images will be described below.

(Line-of-Sight Inference Unit)

The line-of-sight inference unit 130 infers a direction of a line of sight on the basis of the corneal reflection images and the position of the pupil on the image detected by the image processing unit 120. The process of inferring the direction of the line of sight may be performed using an existing inference technique that uses the corneal reflection images and the position of a pupil. For example, a corneal reflection method in which light is radiated from a light source onto an eyeball of a user and positions of a beam of the light reflected on a surface of a cornea and a pupil are detected to infer a direction of a line of sight may be used.

<3. Line-of-Sight Detection Method>

Figure 7:
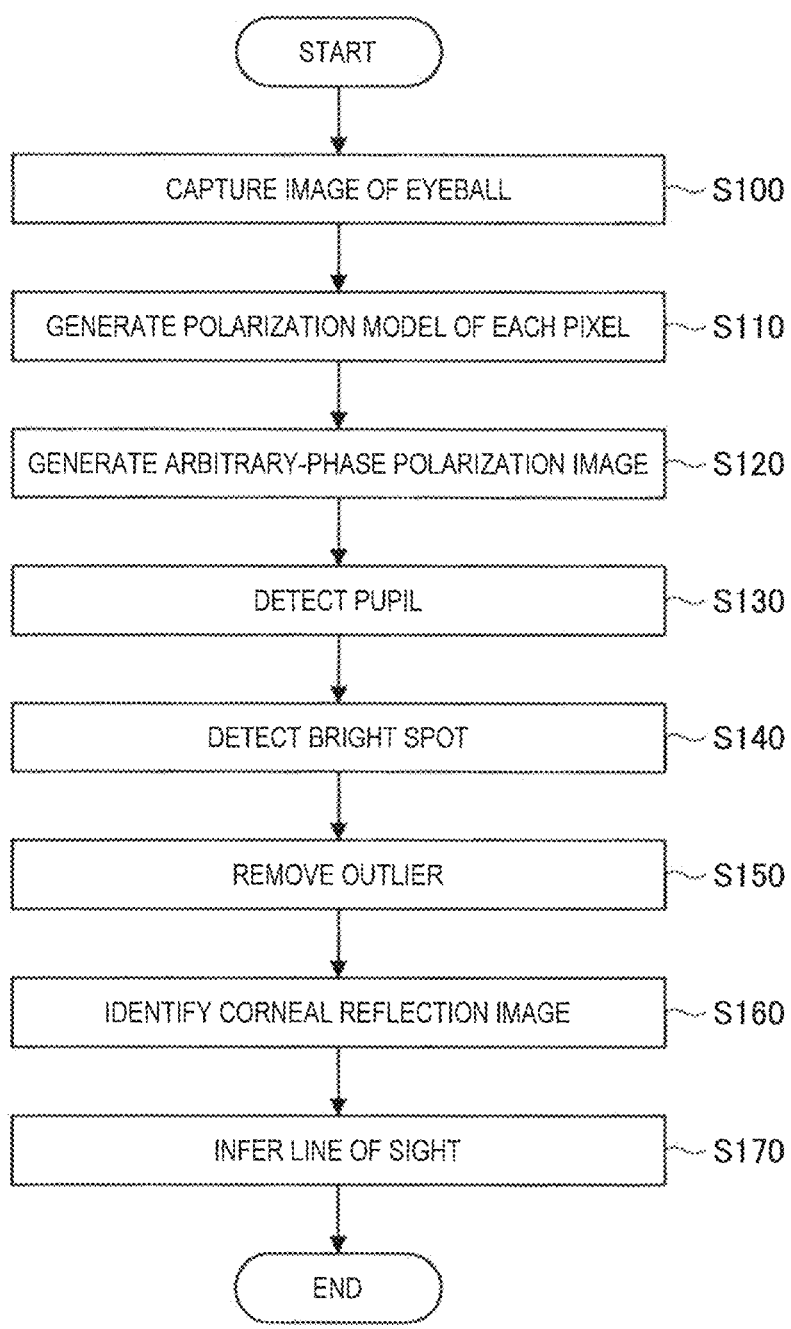
FIG. 7 is a flowchart showing a line-of-sight detection method performed by the eyeball observation device according to the embodiment.

A line-of-sight detection method performed by the eyeball observation device 1 according to the present embodiment will be described below on the basis of FIG. 7. Note that FIG. 7 is a flowchart showing the line-of-sight detection method performed by the eyeball observation device 1 according to the present embodiment.

(S100: Acquisition of Image)

In the line-of-sight detection method according to the present embodiment, first, the imaging device 13 captures an image of an eyeball of a user in a state in which the eyeball is irradiated with infrared light from the infrared light sources 11 (S100). The imaging device 13 according to the present embodiment simultaneously acquires polarized infrared light with three or more directions. The imaging device illustrated in FIG. 5, for example, can simultaneously acquire polarization images of four directions.

(S110: Generation of Polarization Model)

Next, the polarization model generation unit 111 generates a polarization model of each pixel on the basis of the images captured by the imaging device 13 (S110). It is known that, if polarization images with three or more directions acquired by the imaging device 13 according to the present embodiment are used, each pixel can be modeled with a cosine function as shown in Formula (1) below using luminance values and polarization directions of the polarization image. If there are polarization images with three or more directions in principle, a cosine function can be expressed (e.g., refer to the specification of JP 4974543B).

Note that, in Formula (1), I represents a luminance value, $I_{max}$ represents a maximum luminance value, and $I_{min}$ represents a minimum luminance value. In addition, $\theta_{pol}$ represents a polarization angle of a polarization plate of the imaging device 13, and $\varphi$ represents a polarization angle of infrared light.

[Math. 1]

$$I = \frac{I_{max} + I_{min}}{2} + \frac{I_{max} - I_{min}}{2}\cos(2\theta_{pol} - 2\phi) \quad (1)$$

Figure 8:
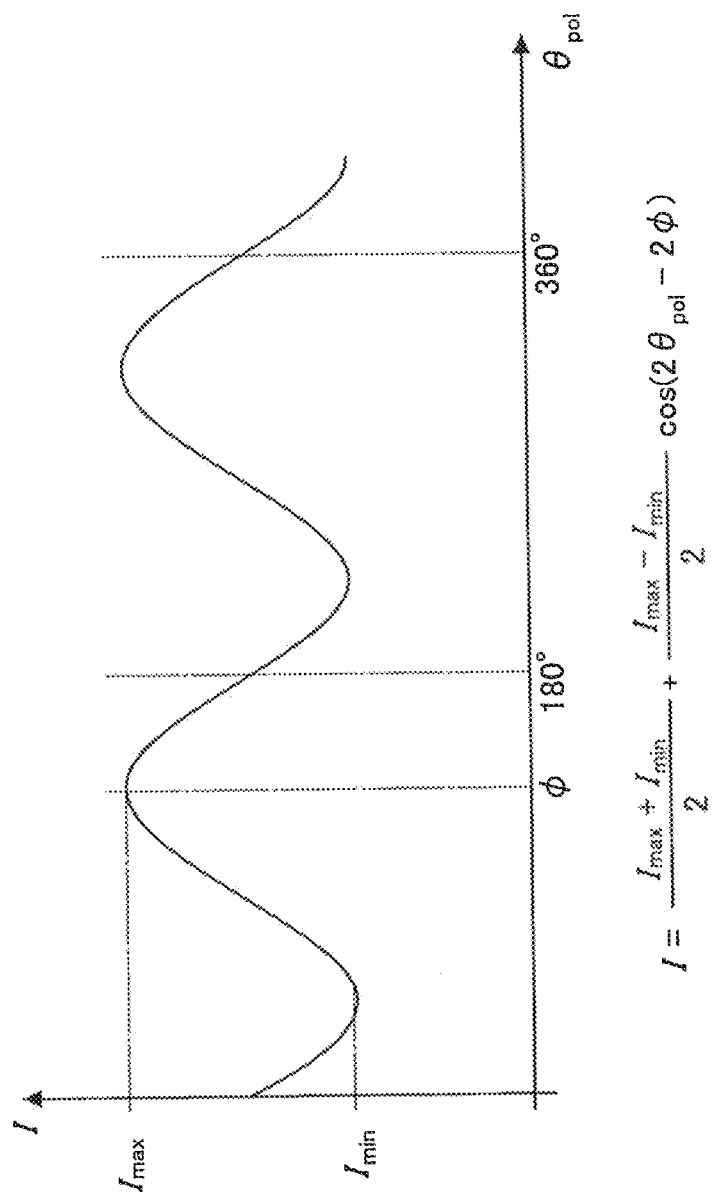
FIG. 8 is a diagram showing a graph of a polarization model of Formula (1).

A graph of the polarization model of Formula (1) depicting a relation between polarization directions and acquired luminance values is shown in FIG. 8. A luminance value of pixels reaches a maximum value at the polarization angle (p (+180°) of infrared light, and a luminance value of pixels reaches a minimum value at an angle deviating ±90° from the polarization angle $\varphi$ as shown in FIG. 8. Here, a polarization direction of the polarization plate at the maximum luminance value is parallel with a polarization direction of infrared light radiated onto the eyeball. In addition, a polarization direction of the polarization plate at the minimum luminance value is perpendicular to a polarization direction of infrared light radiated onto the eyeball.

When the polarization model of each pixel is generated, the polarization model generation unit 111 records the polarization model in the polarization model storage unit 113 and outputs the polarization model to the arbitrary-phase polarization image generation unit 115. Note that, in a case in which the eyeball observation device 1C having the configuration illustrated in FIG. 4 in which the optical path separation device 15 is provided is used, a predetermined process is performed on the assumption of a polarization state affected by the optical path separation device 15 to generate a polarization model. In addition, a polarization model may be generated using, for example, machine learning, other than in the setting based on the above-described Formula (1).

(S120: Generation of Arbitrary-Phase Polarization Image)

Next, the arbitrary-phase polarization image generation unit 115 generates an arbitrary-phase polarization image on the basis of the polarization model of each pixel (S120). The arbitrary-phase polarization image generation unit 115 performs a process of generating an image that is optimal for performing each process in image processing which will be described below. In a case in which a direction of a line of sight of a user wearing glasses is detected, for example, infrared light is reflected on a surface of the glasses and becomes an outlier, and thus it is not possible to detect a pupil or a bright spot normally. In this case, the arbitrary-phase polarization image generation unit 115 generates an image with reduced reflection of glasses, which is noise, performs each detection process on the basis of the image, and thereby the direction of the line of sight of the user wearing glasses can be stably detected.

Figure 9:
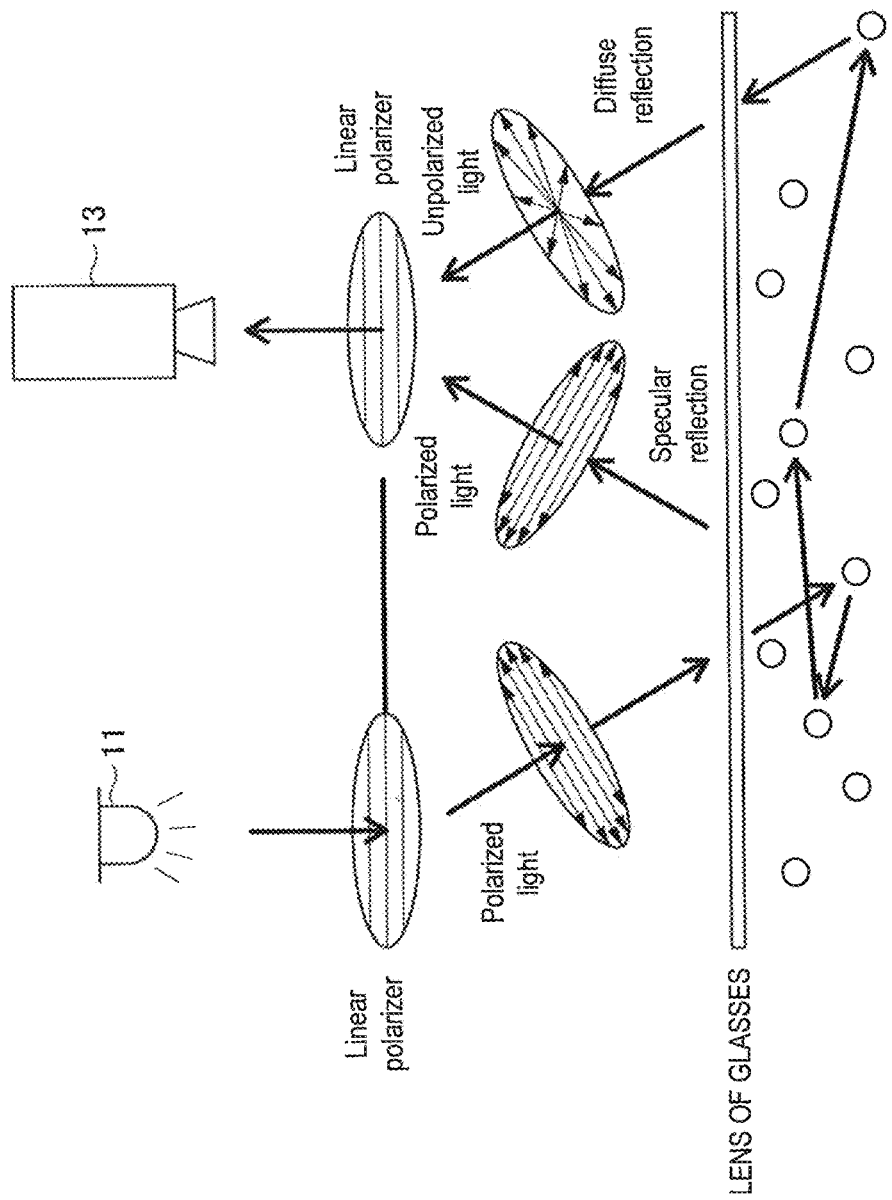
FIG. 9 is an illustrative diagram showing behaviors of polarized light in mirror reflection and diffuse reflection caused by a lens of glasses.

To describe in more detail, if infrared light emitted from the infrared light sources 11 penetrates through the polarizers 12 to become polarized light and then undergoes surface reflection on a surface of a lens of glasses as illustrated in FIG. 9, the reflected light also becomes polarized light traveling in the same polarization direction as polarized light at a time of light incidence on the lens of the glasses. On the other hand, light transmitted through the lens of the glasses repeatedly undergoes diffuse reflection within the lens and becomes unpolarized light. In a case in which the eyeball observation device 1 radiates infrared light onto an eyeball of a user wearing glasses, reflection on the surface of the lens of the gasses includes many mirror reflection components, and polarized light is reflected thereon as it is. Thus, in the present embodiment, the polarizers 12 cause polarization with respect to the infrared light sources 11, polarized light is caused to pass through a polarization plate in a direction in which the polarized light is suppressed, and then a polarization image is obtained by capturing an image of the eyeball using the imaging device 13. Accordingly, mirror reflection components of the polarized light on the surface of the lens of the glasses are reduced and only internal reflection components (i.e., reflection components with respect to the eyeball) can be extracted.

Using the above-described principle, the arbitrary-phase polarization image generation unit 115 generates a polarization image with an optimal phase for detecting a pupil and a bright spot so that a pupil and a bright spot can be detected normally.

For example, by generating a pixel having a minimum luminance value in the polarization model of each pixel generated in Step S110 with respect to the user wearing the glasses, an image for which a polarization direction of the infrared light source 11 is suppressed most, i.e., an image for which reflection of glasses is suppressed, can be generated. Note that it is not necessary to cause a polarization direction of the polarizer of the infrared light source 11 to match a polarization direction of the polarization plate of the imaging device 13 in order to use the polarization model to generate an arbitrary-phase polarization image.

In normal capturing, an edge of a pupil is hidden due to reflection of glasses in a state in which reflection of glasses occurs, which makes it difficult to detect the pupil in image processing. According to the present embodiment, however, the arbitrary-phase polarization image generation unit 115 generates an image from which reflection of glasses has been removed, thus the pupil can be detected therein, and thus a pupil of a user wearing glasses can be reliably detected.

A corneal reflection image to be used in inference of a line of sight is also caused by mirror reflection that occurs on a surface of a cornea. Thus, in order to observe a corneal reflection image with high precision, an image having a phase in which a polarization direction of the infrared light source 11 is not completely suppressed may be generated. Note that a corneal reflection image and a luminance value and a size of reflection of glasses depend on an amount of light of the infrared light source 11. Thus, the arbitrary-phase polarization image generation unit 115 may generate an image that is optimal for the above-described condition.

In addition, in a case in which detection of a bright spot is performed with respect to a user wearing glasses, reflection of glasses and reflection of a cornes exist together, and thus an image generated for detection of a pupil of which each pixel has a minimum luminance value may be used. In such an image, polarization 26 models of reflection of glasses and reflection of a cornea are differently observed due to refraction that occurs when light passes through a lens of the glasses and diffuse reflection that occurs between the glasses and an eyeball. For this reason, even in a case in which a luminance model with a minimum pixel is created using each of pixels, reflection of a corneal is observed with higher luminance than in reflection of glasses. Therefore, a bright spot having a higher luminance value than surrounding spots and satisfying predetermined conditions in terms of size and position may be detected as a corneal reflection image in the image generated for detection of a pupil. Machine learning may be used in this detection.

Note that, before the arbitrary-phase polarization image generation unit 115 performs the process of removing reflection of glasses, bright spots may be roughly detected using features including, for example, sizes, luminance values, positions, edges, circularities, and the like of the bright spots, regions to be processed are limited to pixels of candidate bright spots, and then a polarization image may be generated. Accordingly, an amount of process to be performed by the arbitrary-phase polarization image generation unit 115 can be reduced. In addition, an average image with all polarization directions, for example, may be used in the rough detection of bright spots, and machine learning, for example, may be used in the process.

On the other hand, with respect to a user with naked eyes, the arbitrary-phase polarization image generation unit 115 may generate a polarization image for pupil detection and a polarization image for bright spot detection and use the images as image for detection processes, as in the above-described process for the user wearing glasses. That is, the polarization image for pupil detection may be an image including a minimum luminance value by extracting a minimum luminance value by changing a polarization direction of each pixel of the polarization image using the polarization model, as in the above-described case of the user wearing glasses.

However, an amount of light of an image in which reflection of glasses is suppressed is reduced by half. Thus, for example, a user wearing glasses and a user with naked eyes are distinguished, an image in which reflection of glasses is used for the user wearing glasses, a polarization image with three or more directions is used for the user with naked eyes, and thereby a polarization image for pupil detection may be generated.

Distinguishing a user wearing glasses from a user who is not may be performed using, for example, a characteristic that is a luminance value found in an eye region part of an input image because a region that is supposed to have eyes is normally observed with high luminance if reflection of glasses occurs. Alternatively, infrared light polarized by the polarizers 12 and undergoes mirror reflection on a surface of glasses becomes polarized light, and thus the distinguishment may be performed using a characteristic of a size of a region that has a high degree of polarization in the polarization model on the basis of the degree of polarization expressed by Formula (2) which will be described below. Using the above-described characteristics as input, users who is wearing or not wearing glasses can be distinguished through threshold processing, machine learning, or the like.

In addition, the polarization image for bright spot detection may be acquired as follows with a known polarization direction of a light source. First, in a case in which there are a plurality of light sources, polarization is caused to occur in different directions with respect to all of the light sources. Then, by generating pixels with a polarization direction of a light source that is desired to observe with respect to each of pixels, a polarization image in which outlier and reflection of other light sources are suppressed and which has a luminance value at which reflection of the observed light source on a cornea is significant is generated. Thereafter, the bright spot detection unit 123 of the image processing unit 120 performs a bright spot detection process on the basis of the generated polarization image and sets a bright spot having a detected luminance value higher than or equal to a predetermined threshold value as a real corneal reflection image with respect to the corresponding light source. At this time, in a case in which a plurality of bright spots having luminance values higher than or equal to the predetermined threshold value are detected, a bright spot having a highest luminance value is selected as a real corneal reflection image. Detection of bright spots performed by the bright spot detection unit 123 may be performed using machine learning.

In the case in which there are a plurality of light sources, the arbitrary-phase polarization image generation unit 115 generates the same number of polarization images for bright spot detection as the number of light sources, and the bright spot detection unit 123 detects bright spots on the basis of the polarization images. Note that, when the polarization images for bright spot detection are created, bright spots may be roughly detected using features including, for example, sizes, luminance values, positions, edges, circularities, and the like of the bright spots before the arbitrary-phase polarization image generation unit 115 performs the process of removing reflection of glasses, regions to be processed are limited to pixels of candidate bright spots, and then a polarization image may be generated, as in the above-described case of the user wearing glasses. Accordingly, an amount of process to be performed by arbitrary-phase polarization image generation unit 115 can be reduced. In addition, an average image with all polarization directions, for example, may be used in the rough detection of bright spots, and machine learning for example, may be used in the process.

After the arbitrary-phase polarization image generation unit 115 generates polarization images for pupil detection and polarization images for bright spot detection using the polarization model on the basis of a pre-set condition, the polarization images are recorded in the arbitrary-phase polarization image storage unit 117.

(S130: Detection of Pupil)

When various arbitrary-phase polarization images are generated in Step S120, image processing is performed on the generated polarization images by the image processing unit 120, a pupil and a corneal reflection image are acquired. First, the pupil detection unit 121 detects a pupil in a polarization image for pupil detection having a phase proper for detecting a pupil (S130). In a case in which the infrared light source 11 is disposed at a position distant from an optical axis of the imaging device 13, for example, a pupil included in an acquired captured image is observed to be black (a dark pupil). Alternatively, in a case in which the infrared light source 11 is installed at a position very close to the imaging device 13 on the optical axis thereof, the pupil is observed to be white (a bright pupil) due to retroreflection of a retina. Using the above-described features, the pupil detection unit 121 detects, for example, an elliptical black region (or white region) in the polarization image for pupil detection as a pupil. Alternatively, the pupil detection unit 121 may extract a pupil portion from a difference image of the bright pupil and the dark pupil.

(S140: Detection of Bright Spot)

Next, the bright spot detection unit 123 detects bright spots on the basis of the polarization image for bright spot detection (S140). The bright spot detection unit 123 detects regions of the image having higher luminance values than surrounding regions and sizes equal to or smaller than a predetermined size and of which detection positions have a predetermined degree or more of matching with an installation position of the infrared light source 11 as bright spots. The bright spots detected by the bright spot detection unit 123 also include an outlier such as a pseudo bright spot other than corneal reflection images.

(S150: Removal of Outlier)

Then, the outlier removal unit 125 removes an outlier such as a pseudo bright spot from the respective bright spots detected by the bright spot detection unit 123 and thereby a real corneal reflection image is detected (S150). Outliers include a bright spot appearing through reflection on a sclera rather than a cornea of an eyeball, a bright spot appearing through reflection of lower eyelashes of a user, and the like. In addition, outliers include reflection of light reflected from an environment on an eyeball, reflection of sunlight, and the like. These are elements that hinders a real corneal reflection image from being detected, and thus are removed by the outlier removal unit 125.

The outlier removal unit 125 obtains a degree of polarization ρ using the polarization model stored in the polarization model storage unit 113 with respect to pixels of each bright spot region detected by the bright spot detection unit 123 and removes the outlier on the basis of a magnitude of the degree of polarization ρ. The degree of polarization ρ indicates a degree of linear polarization of observed light, and can be expressed by the following Formula (2).

[Math. 2]

$$\rho = \frac{I_{max} - I_{min}}{I_{max} + I_{min}} \quad (2)$$

Figure 10:
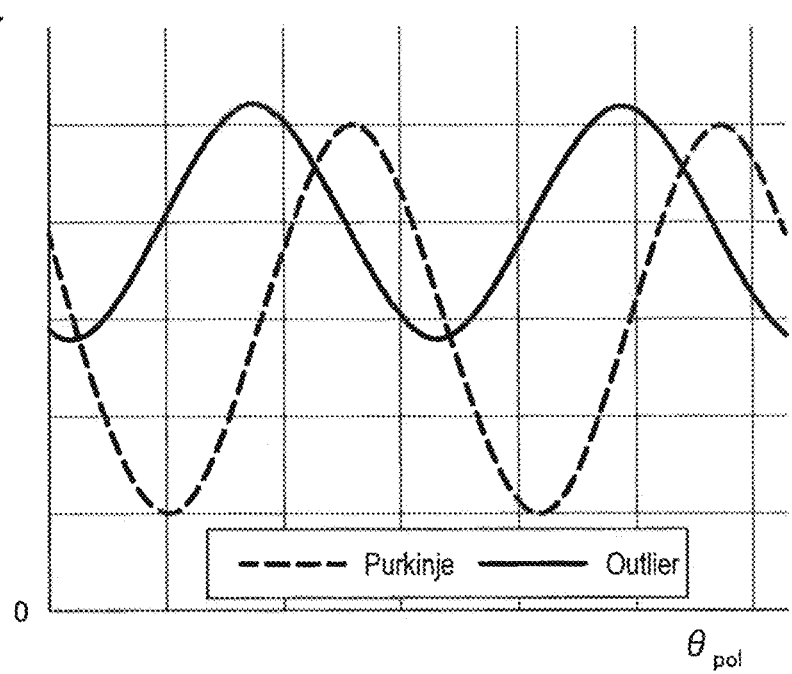
FIG. 10 is a graph showing polarization models of a corneal reflection image and an outlier.

In the present embodiment, the corneal reflection image a reflection image with respect to a surface of a cornea of polarized light that has passed through the polarizers 12, and a degree of polarization ρ thereof increases. On the other hand, a degree of polarization ρ of reflection of sunlight, which is unpolarized light, or reflection on a sclera decreases. Here, FIG. 10 shows an example of a polarization model having a high degree of polarization ρ observed in the corneal reflection image and a polarization model having a low degree of polarization ρ observed in the outlier. As shown in FIG. 10, amplitude of the polarization model of the outlier having the low degree of polarization ρ is smaller than amplitude of the polarization model of the corneal reflection image having the high degree of polarization ρ.

Using the characteristics, the outlier removal unit 125 obtains a degree of polarization ρ on the basis of the above-described Formula (2) and classifies the bright spots detected in Step S140 into real corneal reflection images and outliers using threshold processing or machine learning. In threshold processing, for example, if a value of the degree of polarization ρ of a bright spot is smaller than a predetermined value, the bright spot is classified as an outlier, and if the a value of the degree of polarization ρ of the bright spot is higher than or equal to the predetermined value, the bright spot is classified as a real corneal reflection image.

(S160: Identification of Corneal Reflection Image)

Thereafter, the corneal reflection image identification unit 127 identifies a corresponding infrared light source 11 to the real corneal reflection image specified by the outlier removal unit 125 to ascertain which light source has contributed to generation of the reflection image (S160). The process of Step S160 may be executed only in a case in which a plurality of infrared light sources 11 radiate infrared light onto the eyeball E.

Figure 11:
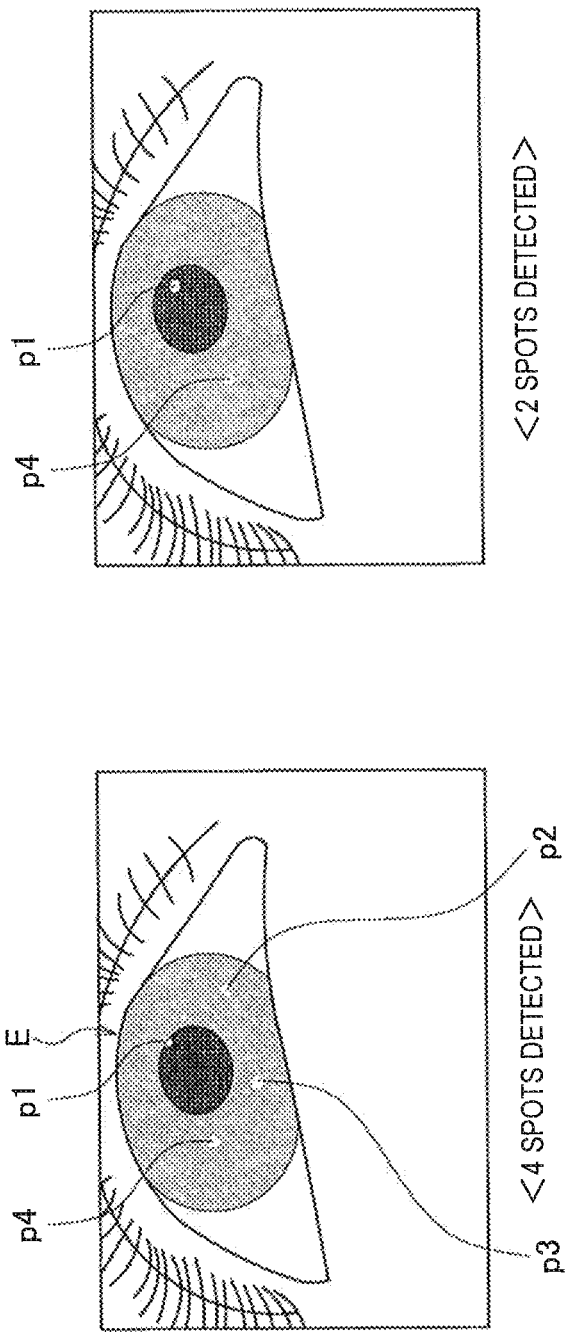
FIG. 11 shows illustrative diagrams showing a difference in observation points between corneal reflection images.

In inference of a line of sight using corneal reflection, accuracy in inference of a line of sight can be improved or non-observation of a corneal reflection image caused by a position of the line of sight can be prevented by using a plurality of the infrared light sources 11. However, when four infrared light sources 11 radiate infrared light onto the eyeball E, for example, four corneal reflection images p1 to p4 are supposed to be detected as illustrated on the left part of FIG. 11, but only two corneal reflection images p1 and p4 may be detected as illustrated on the right part of FIG. 11. In the case in which only some of a plurality of corneal reflection images are observed as described above, it may be difficult to exactly identify a light source corresponding to a reflection image. Thus, in the present embodiment, a principle in which a difference in polarization directions leads to a phase difference of polarization models is applied and thereby each infrared light source 11 corresponding to a corneal reflection image is identified.

Figure 12:
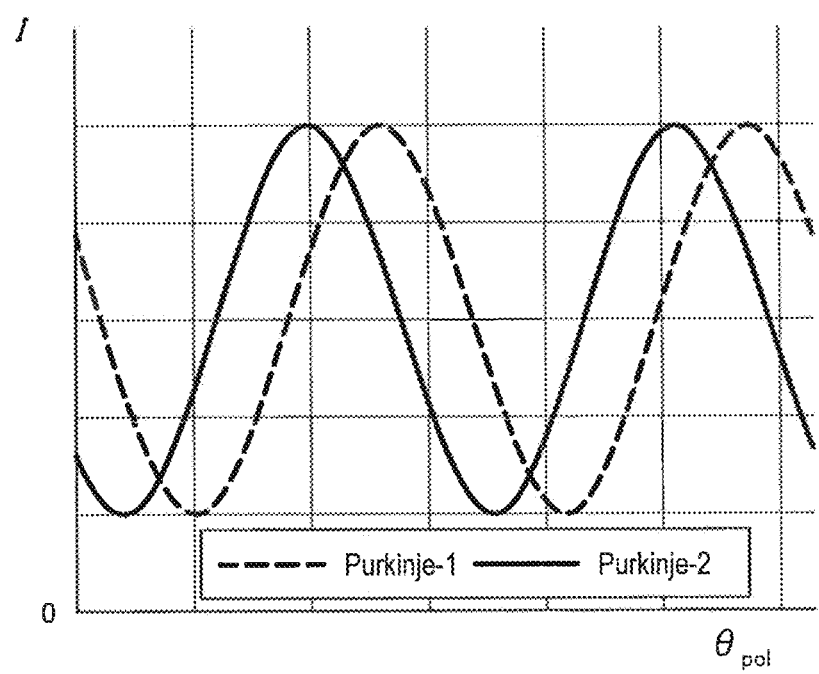
FIG. 12 is a graph showing polarization models of reflection of infrared light sources (corneal reflection images) having different polarization directions.

To describe in more detail, first, the eyeball observation device 1 according to the present embodiment is configured to differ polarization directions of the polarizers 12 installed corresponding to each of the infrared light sources 11 to enable the infrared light sources 11 to be specified. In addition, the polarization model generation unit 111 of the image generation unit 110 generates polarization models of each of the infrared light sources 11 and records the polarization models in the polarization model storage unit 113. Here, a polarization angle $\theta_{pol}$ of the polarization plate of the imaging device 13 is meaningful only in the range of $0°≤\theta_{pol}<180°$ in principle, polarization directions of the infrared light sources 11 are exclusively determined within this range. When polarization directions of two infrared light sources 11 are set to differ from each other, for example, a polarization model of a first infrared light source (Purkinje-1) and a polarization model of a second infrared light source (Purkinje-2) have the same amplitude and cycle but different phases as shown in, for example, FIG. 12.

In addition, the corneal reflection image identification unit 127 identifies corneal reflection images using degrees of phase similarity of the polarization model of the infrared light source 11 and the polarization model of each observed corneal reflection image. That is, identification is performed on the assumption that an infrared light source 11 and a corneal reflection image having similar phases and high degrees of phase similarity correspond to each other. Degrees of phase similarity may be identified through threshold processing or using machine learning. Note that a polarization direction of the infrared light source 11 may be obtained through calibration in advance or may be set when all bright spots are observed and easily and exactly identified at a time of inference of a line of sight. In the calibration, the polarization model of the observed corneal reflection image is obtained and a phase of this polarization model is recorded in a light source polarization direction storage unit 20 in association with each infrared light source 11. Since disposition of the polarizers 12 is decided at the time of assembly of the eyeball observation device 1, calibration may be basically performed one time.

(S170: Inference of Line of Sight)

Then, the line-of-sight inference unit 130 infers a direction of a line of sight on the basis of the corneal reflection image and a pupil position in the image detected by the image processing unit 120 (S170). For example, the line-of-sight inference unit 130 infers three-dimensional coordinates of the center of the radius of the corneal curvature from the corneal reflection image on the image observed with known installation positions of the infrared light sources 11 and the imaging device 13. In addition, the line-of-sight inference unit 130 inters three-dimensional coordinates of the center of a pupil from the pupil position on the image and obtains an optical axis of the eyeball as an axis connecting the positions indicated by the coordinates. Then, the line-of-sight inference unit 130 performs a process of converting the optical axis obtained from the observed information into an axis of sight corresponding to the direction of the line of sight of a person and thereby obtains a three-dimensional line-of-sight vector. Alternatively, the line-of-sight inference unit 130 may obtain a line-of-sight vector by mapping a two-dimensional vector connecting the corneal reflection image and the pupil on the image to a line-of-sight position on a display. A line-of-sight inference technique for inferring a line of sight using the line-of-sight detection method according to the present embodiment is not particularly limited, and any of various existing line-of-sight inference technique can be used.

The line-of-sight detection method according to the present embodiment has been described above. According to the present embodiment, when a pupil or a corneal reflection image is detected to perform inference of a line of sight, polarization images appropriate for the detection are used, and thus a pupil or a corneal reflection image can be detected with higher accuracy. In addition, the imaging device 13 of the eyeball observation device 1 according to the present embodiment simultaneously acquires polarization images with three or more directions, and thus polarization images for pupil detection and polarization images for bright spot detection can be simultaneously generated using polarization models of pixels generated on the basis of the polarization images. In addition, even in a case in which a line of sight of a user wearing glasses is detected, mirror reflection that occurs on a lens of the glasses can be removed.

Furthermore, outliers other than corneal reflection image can be removed and association of corneal reflection images with infrared light sources 11 in a case in which a plurality of infrared light sources are used can also be exactly performed using the polarization models. As described above, inference of a line of sight can be performed stably and accurately using the line-of-sight detection method according to the present embodiment. In addition, precise alignment of a polarization direction of the infrared light source 11 with a polarization direction of the polarization plate of the imaging device 13 is not necessary, and application of the method to various kinds of equipment and situations is easily possible. Note that an object to be noted may be specified using an imaging device other than the imaging device 13, or an alert may be issued in a case in which an object to be noted has deviated from a direction of a line of sight.

Modified Example

The eyeball observation device according to the present embodiment is not limited to use in inference of a line of sight and may be used in an application that images a state of an eyeball. According to the eyeball observation device of the present embodiment, for example, by determining an index or a sign to be described below on the basis of a state of an imaged eyeball, a health state or an awakened state of a user can be determined or inferred. An eyeball observation device of the present embodiment as a modified example may have an eyeball state inference arithmetic device instead of or in addition to the line-of-sight inference arithmetic device. Note that the eyeball state inference arithmetic device may be regarded as a device configured to acquire information of an eyeball state from a captured eyeball image and determine an index or a sign which will be described below.

According to the eyeball observation device of the present embodiment, an image in which reflection of glasses is suppressed and a pupil and an iris can be easily detected can be generated. Note that iris authentication is a technology of identifying a person using a pattern of the person's iris. It is necessary in iris authentication as well to acquire eyeball information with respect to a pupil, an iris, or the like.

In addition, according to the eyeball observation device of the present embodiment, a health state or an awakened state of a person can be inferred by observing the diameter of a pupil or handling of an iris. As in the case in which a line of sight is detected, mirror reflection on a lens of glasses can be removed according to the eyeball observation device of the present embodiment. Thus, accuracy in detection of a pupil or an iris of a user can be improved.

A parameter acquired from an eyeball image acquired by the eyeball observation device of the present embodiment is compared with various indices relating to a health state, and thereby the health state may be determined or inferred. For example, mydriasis and miosis of a pupil are caused by interaction between a sympathetic nerve and a parasympathetic nerve system. Thus, a change in mydriasis and miosis of a pupil may be used as an index indicating a state of an autonomic nerve system. For example, mydriasis of 5 mm or larger may be used as an index of hypoglycemia, hypoxia, drug intoxication, a line of a midbrain, cerebral herniation, cardiac arrest, or the like. Miosis of 2 mm or smaller may be used as a sign of an initial stage of cerebral herniation, organophosphate poisoning, or the like. A pinhole of 1 mm or smaller may be used as a sign of pontine hemorrhage, narcotic intoxication, or the like. In a case in which left and right pupils have a difference of 0.5 mm or greater in diameter, it may be regarded as a sign of cerebral herniation. Note that mydriasis and miosis can be measured by exactly extracting contour of a pupil from an eyeball observation image and measuring the diameter of the pupil.

In addition, it is regarded that a health state can be understood by observing a state of an iris (iridology). For example, high blood cholesterol or a lipid metabolism problem can be determined or inferred by observing a degree of haze around an iris (a cholesterol ring). Thus, a health state of a user may be determined or inferred on the basis of the degree of haze around the iris. In addition, a state in which one or more sums appear around a pupil indicates a highly stressed state. Thus, in the case in which one or more sums appear, a user may be determined or inferred to be in a highly stressed state.

Furthermore, according to the eyeball observation device of the present embodiment, an awakened state of a person can also be inferred by observing the person's eyeball. A degree of fatigue, work efficiency, or the like can be ascertained on the basis of a change in an awakened state. In particular, ascertaining a degree of awakening of a driver of a car, a train, or the like may be very effective to ensure safety. A pupil contracts when, for example, a degree of awakening becomes lower and an action of a parasympathetic nerve system has superiority to that of a sympathetic nerve, however, mydriasis that counters miosis is repeated in the meantime. Thus, in a case in which a degree of awakening becomes lower, the diameter of a pupil exhibits large fluctuation at a low frequency (large low frequency fluctuation). Therefore, a health state or an awakened state may be determined or inferred on the basis of a change in the diameter of a pupil.

Note that, if two polarization imaging devices are used, a distance to an eyeball can be measured using triangulation and thereby the diameter of the pupil can be accurately measured. In addition, in a case in which ordinary changes in the diameter of a pupil of a person are observed, relative changes in the diameter of the pupil can be observed and a health state and an awakened state can be managed only with one imaging device by normalizing a part of a face such as an outer corner or an inner corner of an eye while using the part as a mark through image processing.

As described above, various states of a user can be ascertained by observing the user's eyeball. According to the present embodiment, an eyeball image from which reflection on a surface of glasses is removed can be generated with respect to a user wearing glasses. Person identification and daily health check can be performed through iris authentication by, for example, incorporating an imaging device and a polarized infrared light source into a smartphone. With this device configuration, not only determination or inference of a health state or an awakened state but also detection of a line of sight of a user can be performed. In addition, awakened states may be monitored by installing polarized infrared light sources and infrared cameras at positions at which eyeballs can be observed in vehicles such as cars, trains, or airplanes which need operators.

According to the eyeball observation device of the present embodiment, eyeball images can be acquired with the same configuration also for users with naked eyes. There are general cases in which illumination is insufficient due to light, which is incident on an image sensor, being limited by a polarization plate. In a case in which a sensor which simultaneously acquires three or more polarization directions is used, insufficient illumination can be resolved by using average images of all polarization directions.

<4. Hardware Configuration>

Figure 13:
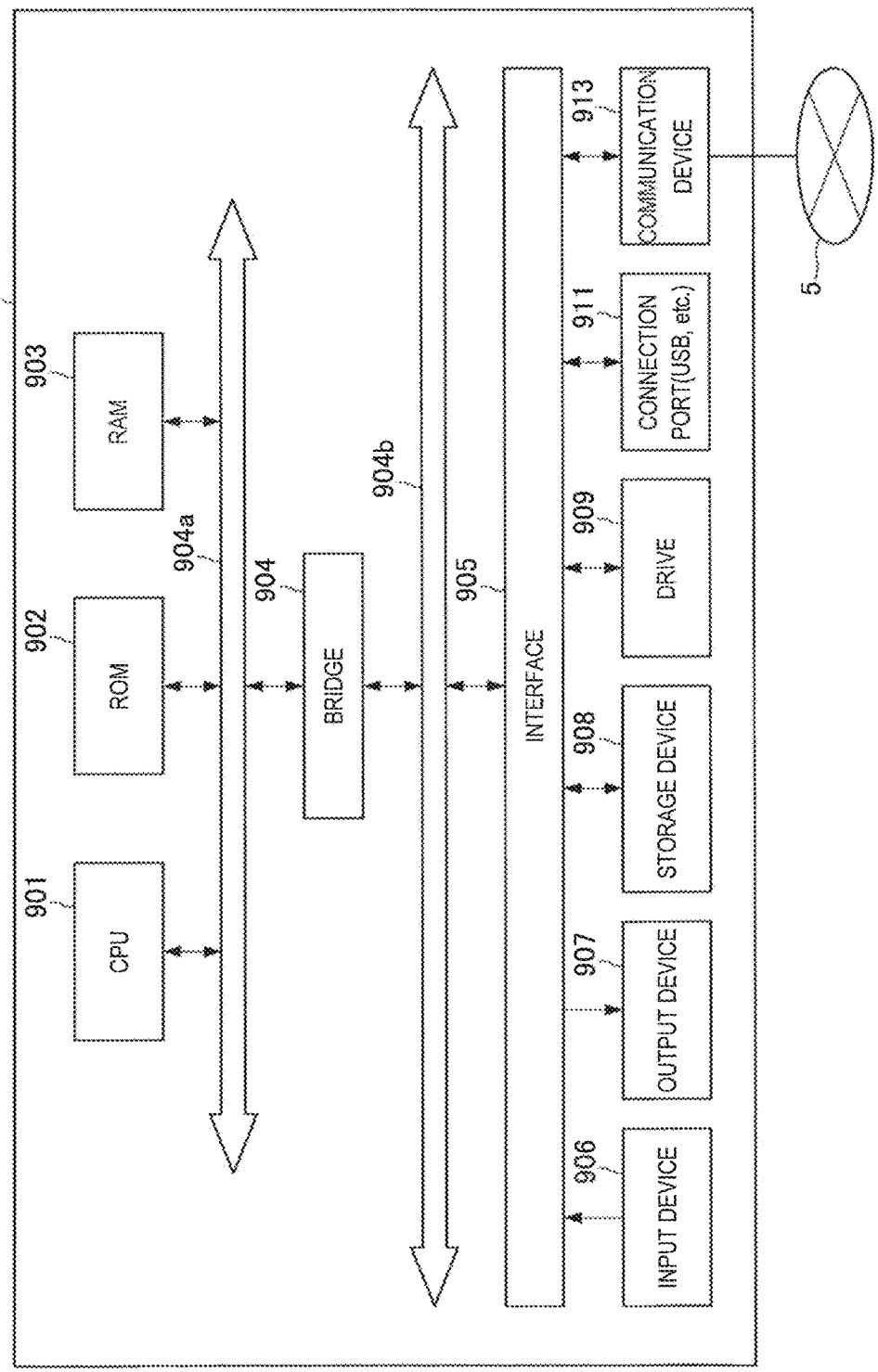
FIG. 13 is a hardware configuration diagram showing a hardware configuration of the line-of-sight inference arithmetic device according to the embodiment.

Finally, the hardware configuration example of the line-of-sight inference arithmetic device 100 according to the embodiment described above is described. FIG. 13 is a hardware configuration diagram illustrating the hardware configuration of the line-of-sight inference arithmetic device 100 according to the embodiment described above.

The line-of-sight inference arithmetic device 100 according to the present embodiment can be implemented as a processing device including a computer, as described above. As illustrated in FIG. 13, the line-of-sight inference arithmetic device 100 is configured to include a central processing unit (CPU) 901, a read only memory (ROM) 902, a random access memory (RAM) 903, and a host bus 904*a*. In addition, the line-of-sight inference arithmetic device 100 is configured to include a bridge 904, an external bus 904*b*, an interface 905, an input device 906, an output device 907, a storage device 908, a drive 909, a connection port 911, and a communication device 913.

The CPU 901 functions as an arithmetic processing unit and a control unit and controls the overall operation in the line-of-sight inference arithmetic device 100 in accordance with various programs. In addition, the CPU 901 may be a microprocessor. The ROM 902 stores, in one example, a programs or an operation parameter that is used by the CPU 901. The RAM 903 temporarily stores a program used in the execution by the CPU 901 or a parameter or the like that appropriately changes during the execution. These components are interconnected via the host bus 904*a* composed of a CPU bus or the like.

The host bus 904*a* is connected to the external bus 904*b* such as peripheral component interconnect/interface (PCI) bus through the bridge 904. Moreover, the host bus 904*a*, the bridge 904, and the external bus 904*b* are not necessarily configured as separate components, and the functions of them may be incorporated into a single bus.

The input device 906 is configured to include input means through which the user can input information and an input control circuit that generates an input signal on the basis of the input by the user and outputs it to the CPU 901. An example of the input means includes a mouse, a keyboard, a touch panel, a button, a microphone, a switch, and a lever. The output device 907 includes, in one example, a display device such as a liquid crystal display (LCD) device, an organic light emitting diode (OLED) device, or a lamp, and a speech output device such as a speaker.

The storage device 908 is an example of the storage unit of the line-of-sight inference arithmetic device 100 and is a device for storing data. The storage device 908 may include a recording medium, a recording device that records data in the recording medium, a readout device that reads out data from the recording medium, and a deletion device that deletes data recoded in the recording medium. The storage device 908 drives a hard disk, and stores a program executed by the CPU 901 and various kinds of data.

The drive 909 is a reader-writer for a recording medium, and is built in the line-of-sight inference arithmetic device 100 or is externally attached thereto. The drive 909 reads out information recorded in a mounted magnetic disk, optical disk, magneto-optical disc, or removable storage medium such as a semiconductor memory, and outputs the information to the RAM 903.

The connection port 911 is an interface connected to an external device and is a port for connecting an external device that is capable of transmitting data through, in one example, a universal serial bus (USB). Furthermore, the communication device 913 is, in one example, a communication interface composed of a communication device or the like for connecting to a communication network 5. Furthermore, the communication device 913 may be a communication device compatible with a wireless local area network (LAN), a communication device compatible with a wireless USB, or a wired communication device that communicates with wire.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Although association of corneal reflection images with infrared light sources when the plurality of infrared light sources are used is made by executing calibration in the above-described embodiment, for example, the present technology is not limited thereto. In a case in which deviation of angles of polarizers corresponding to respective infrared light sources is known, association with corneal reflection images may be made on the basis of angles of polarization directions caused by the polarizers.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An eyeball observation device including:

at least one infrared light source configured to radiate polarized infrared light onto an eyeball of a user, and at least one imaging device configured to capture an image of the eyeball irradiated with the polarized infrared light and to be capable of simultaneously capturing a polarization image with at least three directions.

(2)

The eyeball observation device according to (1), including:

a polarization model generation unit configured to generate a polarization model representing a relation between a polarization direction and luminance with respect to each pixel of the polarization image acquired by the imaging device.

(3)

The eyeball observation device according to (2), including:

an arbitrary-phase polarization image generation unit configured to generate an arbitrary-phase polarization image having an arbitrary polarization direction from the polarization image acquired by the imaging device by using the polarization model.

(4)

The eyeball observation device according to (3), in which the arbitrary-phase polarization image generation unit extracts a minimum luminance value by changing a polarization direction with respect to each pixel of the polarization image and generates a polarization image for pupil detection having the minimum luminance value.

(5)

The eyeball observation device according to (3) or (4), in which the arbitrary-phase polarization image generation unit extracts a maximum luminance value by changing a polarization direction with respect to each pixel of the polarization image and generates a polarization image for bright spot detection having the maximum luminance value.

(6)

The eyeball observation device according to (5), including:

a bright spot detection unit configured to detect a bright spot in the polarization image for bright spot detection; and an outlier removal unit configured to remove an outlier of a corneal reflection image by the bright spot on the basis of degrees of polarization of detected bright spots.

(7)

The eyeball observation device according to (6), in which the outlier removal unit removes a bright spot having the degree of polarization smaller than a predetermined value as an outlier among the detected bright spots.

(8)

The eyeball observation device according to (6) or (7), including:

a corneal reflection image identification unit configured to identify the infrared light source corresponding to a corneal reflection image acquired by removing an outlier by the outlier removal unit on the basis of a difference between phases of the polarization models.

(9)

The eyeball observation device according to any one of (1) to (8), in which, in a case in which the plurality of infrared light sources are provided, at least one of polarizers corresponding to the respective infrared light sources has a polarization direction different from polarization directions of the other polarizers.

(10)

The eyeball observation device according to any one of (1) to (9), further including:

a first arithmetic device configured to detect or infer a line of sight of the user on the basis of the captured image of the eyeball.

(11)

The eyeball observation device according to any one of (1) to (10), further including:

a second arithmetic device configured to acquire eyeball state information on the basis of the captured image of the eyeball and detect or infer at least one of a health state and an awakened state of the user on the basis of the acquired eyeball state information.

(12)

An eyewear terminal including:

a lens configured to be provided in front of an eye of a user, and an eyeball observation device including at least one infrared light source configured to radiate polarized infrared light onto an eyeball of the user and at least one imaging device configured to capture an image of the eyeball irradiated with the polarized infrared light and to be capable of simultaneously capturing a polarization image with at least three directions.

(13)

The eyewear terminal according to (12), further including:

a first arithmetic device configured to detect or infer a line of sight of the user on the basis of the captured image of the eyeball.

(14)

The eyewear terminal according to (12) or (13), further including:

a second arithmetic device configured to acquire eyeball state information on the basis of the captured image of the eyeball and detect or infer at least one of a health state and an awakened state of the user on the basis of the acquired eyeball state information.

(15)

A line-of-sight detection method including:

capturing an image of an eyeball of a user irradiated with infrared light polarized with respect to the eyeball by at least one infrared light source and simultaneously acquiring a polarization image with at least three directions;

generating a polarization model representing a relation between a polarization direction and luminance with respect to each pixel of the polarization image;

generating an arbitrary-phase polarization image having an arbitrary polarization direction by using the polarization model; and inferring a direction of a line of sight on the basis of the arbitrary-phase polarization image.

(16)

A program causing a computer to execute:

capturing an image of an eyeball of a user irradiated with infrared light polarized with respect to the eyeball by at least one infrared light source and simultaneously acquiring a polarization image with at least three directions;

generating a polarization model representing a relation between a polarization direction and luminance with respect to each pixel of the polarization image;

generating an arbitrary-phase polarization image having an arbitrary polarization direction by using the polarization model; and inferring a direction of a line of sight on the basis of the arbitrary-phase polarization image.

REFERENCE SIGNS LIST 1 eyeball observation device
11 infrared light source
12 polarizer
13 imaging device
15 optical path separation device
20 light source polarization direction storage unit
100 line-of-sight inference arithmetic device
110 image generation unit
111 polarization model generation unit
113 polarization model storage unit
115 arbitrary-phase polarization image generation unit
117 arbitrary-phase polarization image storage unit
120 image processing unit
121 pupil detection unit
123 bright spot detection unit
125 outlier removal unit
127 corneal reflection image identification unit
130 line-of-sight inference unit

The invention claimed is:

1. An eyeball observation device comprising:
   at least one infrared light source configured to radiate polarized infrared light onto an eyeball of a user;
   at least one imaging device configured to capture an image of the eyeball irradiated with the polarized infrared light and to be capable of simultaneously performing capturing with at least three polarization directions in order to capture a polarization image that includes polarization in at least three directions;
   a polarization model generation unit configured to generate a polarization model representing a relation between a polarization direction and luminance with respect to each pixel of the polarization image acquired by the imaging device;
   an arbitrary-phase polarization image generation unit configured to generate an arbitrary-phase polarization image having an arbitrary polarization direction from the polarization image acquired by the imaging device by using the polarization model, wherein the arbitrary-phase polarization image generation unit extracts a maximum luminance value by changing a polarization direction with respect to each pixel of the polarization image and generates a polarization image for bright spot detection having the maximum luminance value;
   a bright spot detection unit configured to detect a bright spot in the polarization image for bright spot detection; and
   an outlier removal unit configured to remove an outlier of a corneal reflection image by the bright spot on the basis of degrees of polarization of detected bright spots,
   wherein the polarization model generation unit, the arbitrary-phase polarization image generation unit, the bright spot detection unit, and the outlier removal unit are each implemented via at least one processor.

2. The eyeball observation device according to claim 1, wherein the arbitrary-phase polarization image generation unit extracts a minimum luminance value by changing a polarization direction with respect to each pixel of the polarization image and generates a polarization image for pupil detection having the minimum luminance value.

3. The eyeball observation device according to claim 1, wherein the outlier removal unit removes a bright spot having the degree of polarization smaller than a predetermined value as an outlier among the detected bright spots.

4. The eyeball observation device according to claim 1, further comprising:
   a corneal reflection image identification unit configured to identify the infrared light source corresponding to a corneal reflection image acquired by removing an outlier by the outlier removal unit on the basis of a difference between phases of the polarization models, wherein the corneal reflection image identification unit is implemented via at least one processor.

5. The eyeball observation device according to claim 1, wherein, in a case in which the plurality of infrared light sources are provided, at least one of polarizers corresponding to the respective infrared light sources has a polarization direction different from polarization directions of the other polarizers.

6. The eyeball observation device according to claim 1, further comprising:
a first arithmetic device configured to detect or infer a line of sight of the user on the basis of the captured image of the eyeball,
wherein the first arithmetic device is implemented via at least one processor.

7. The eyeball observation device according to claim 1, further comprising:
a second arithmetic device configured to acquire eyeball state information on the basis of the captured image of the eyeball and detect or infer at least one of a health state and an awakened state of the user on the basis of the acquired eyeball state information,
wherein the second arithmetic device is implemented via at least one processor.

8. An eyewear terminal comprising:
a lens configured to be provided in front of an eye of a user; and
an eyeball observation device including:
at least one infrared light source configured to radiate polarized infrared light onto an eyeball of the user;
at least one imaging device configured to capture an image of the eyeball irradiated with the polarized infrared light and to be capable of simultaneously performing capturing with at least three polarization directions in order to capture a polarization image that includes polarization in at least three directions;
a polarization model generation unit configured to generate a polarization model representing a relation between a polarization direction and luminance with respect to each pixel of the polarization image acquired by the imaging device;
an arbitrary-phase polarization image generation unit configured to generate an arbitrary-phase polarization image having an arbitrary polarization direction from the polarization image acquired by the imaging device by using the polarization model, wherein the arbitrary-phase polarization image generation unit extracts a maximum luminance value by changing a polarization direction with respect to each pixel of the polarization image and generates a polarization image for bright spot detection having the maximum luminance value;
a bright spot detection unit configured to detect a bright spot in the polarization image for bright spot detection; and
an outlier removal unit configured to remove an outlier of a corneal reflection image by the bright spot on the basis of degrees of polarization of detected bright spots,
wherein the polarization model generation unit, the arbitrary-phase polarization image generation unit, the bright spot detection unit, and the outlier removal unit are each implemented via at least one processor.

9. The eyewear terminal according to claim 8, further comprising:
a first arithmetic device configured to detect or infer a line of sight of the user on the basis of the captured image of the eyeball.

10. The eyewear terminal according to claim 8, further comprising:
a second arithmetic device configured to acquire eyeball state information on the basis of the captured image of the eyeball and detect or infer at least one of a health state and an awakened state of the user on the basis of the acquired eyeball state information.

11. A line-of-sight detection method comprising:
capturing an image of an eyeball of a user irradiated with infrared light polarized with respect to the eyeball by at least one infrared light source and simultaneously performing capturing with at least three polarization directions in order to acquire a polarization image that includes polarization in at least three directions;
generating a polarization model representing a relation between a polarization direction and luminance with respect to each pixel of the polarization image;
generating an arbitrary-phase polarization image having an arbitrary polarization direction by using the polarization model;
extracting a maximum luminance value by changing a polarization direction with respect to each pixel of the polarization image;
generating a polarization image for bright spot detection having the maximum luminance value;
detecting a bright spot in the polarization image for bright spot detection; and
removing an outlier of a corneal reflection image by the bright spot on the basis of degrees of polarization of detected bright spots.

12. A non-transitory computer-readable medium having embodied thereon a program, which when executed by a computer causes the computer to execute a method, the method comprising:
capturing an image of an eyeball of a user irradiated with infrared light polarized with respect to the eyeball by at least one infrared light source and simultaneously performing capturing with at least three polarization directions in order to acquire a polarization image that includes polarization in at least three directions;
generating a polarization model representing a relation between a polarization direction and luminance with respect to each pixel of the polarization image;
generating an arbitrary-phase polarization image having an arbitrary polarization direction by using the polarization model;
extracting a maximum luminance value by changing a polarization direction with respect to each pixel of the polarization image;
generating a polarization image for bright spot detection having the maximum luminance value;
detecting a bright spot in the polarization image for bright spot detection; and
removing an outlier of a corneal reflection image by the bright spot on the basis of degrees of polarization of detected bright spots.

13. The line-of-sight detection method according to claim 11, further comprising:
inferring a direction of a line of sight on the basis of the arbitrary-phase polarization image.

14. The non-transitory computer-readable medium according to claim 12, wherein the further comprises:

inferring a direction of a line of sight on the basis of the arbitrary-phase polarization image.

* * * * *